United States Patent [19]

Mauser et al.

[11] 4,357,944
[45] Nov. 9, 1982

[54] CARDIOTACHOMETER

[76] Inventors: Rudolf Mauser, Haussmannstr. 146B, Stuttgart; Horst Chmiel, Paracelsusstrasse 14, 7250 Leonberg, both of Fed. Rep. of Germany

[21] Appl. No.: 194,955

[22] Filed: Oct. 8, 1980

[30] Foreign Application Priority Data

Oct. 15, 1979 [DE] Fed. Rep. of Germany ....... 2941668

[51] Int. Cl.$^3$ .............................................. A61B 5/02
[52] U.S. Cl. ................................................. 128/663
[58] Field of Search .............................. 128/661, 663

[56] References Cited

U.S. PATENT DOCUMENTS

| | | | |
|---|---|---|---|
| 3,762,221 | 10/1973 | Coulthard | 128/663 |
| 3,763,851 | 10/1973 | Haff et al. | 128/661 |
| 3,910,259 | 10/1975 | Sullivan | 128/661 |
| 3,974,692 | 8/1976 | Hassler | 128/663 |

*Primary Examiner*—William E. Kamm

[57] ABSTRACT

A pair of doppler type ultrasonic transmitters and receiving devices are employed, one operating at a frequency lower than the other. Each of the devices are connected to a demodulator to produce first and second doppler frequency signals, one indicative of vascular blood flow, the other indicative of movement of the vascular wall. The doppler frequencies are fed to a signal processing circuit and a reference stage received as its input, the output of the signal processors. The reference stage produces an output signal on coincidence of the two input signals which is indicative of the heart-beat frequency.

15 Claims, 8 Drawing Figures

CARDIOTACHOMETER

The invention relates to a cardiotachometer for determining the frequency of heartbeats by means of an ultrasonic transmitting and receiving device which works according to the ultrasonic Doppler-principle, with a signal-processing circuit arrangement connected downstream for the purpose of determining a movement of the vascular wall.

Instruments measuring heartbeats of the type cited above are known, for instance, from the German publication of unexamined patent specifications (OS) Nos. 2 219 045 and 2 331 551. By means of these instruments for measuring the frequency of the heartbeat, ultrasound is beamed directly on the heart wall, making it possible to determine the movement of the heart wall directly as a movement of the vascular wall. According to the German patent disclosure (OS) No. 2 219 045 this is achieved by having a selected member of the heartbeat-meter proposed therein connected downstream from its ultrasonic receiver, whereby this selected member permits only those receiving signals to pass to a Doppler-discriminator which originate from one of the two heart pulsation movements, i.e. either from the heart pulsation movement in the direction of the ultrasonic system or from that occurring in the direction away from the ultrasonic system. Connected into the circuit downstream from this Doppler-discriminator is a member which suppresses Doppler-components having a frequency greater than the highest frequency expected from the Doppler-components originating from the movement of the heart wall, followed by an amplitude modulator for the amplitude modulation of the Doppler-signal with limited frequency, a member for suppressing frequencies of the demodulation signal greater than the highest heart frequency to be expected, a differentiator for differentiating the demodulation signal with limited frequency, as well as a pulse generator. The latter delivers a voltage impulse when the signal emitted by the differentiator exceeds a predetermined threshold value.

Measuring of the frequency of the heartbeat according to the German publication of an unexamined patent specification (OS) 2 331 551 occurs however in that way that the Doppler-signals obtained with an ultrasonic transmitting and receiving device are fed to a readout unit, in which three consecutive signals are compared in order to establish a criterion for differentiating between useful signals, i.e. signals corresponding to a heartbeat, and disturbance signals. The readout unit controls a gate circuit, by way of which the useful signals are delivered to an output unit, while the disturbance signals are barred from passing by this gate circuit. The output unit forms a mean value of the useful signals by way of an interval of three heartbeats, in order to obtain an output signal which corresponds to the frequency of heartbeats.

Although in the two instruments for measuring the frequency of the heartbeats pursuant to the German printed publication of unexamined patent specifications (OS) Nos. 2 219 045 and 2 331 551 certain disturbances are eliminated, these heartbeat-meters do not differentiate, however, between systoles and extra-systoles of the heart and also don't permit a separate display of the normal heartbeat frequency, i.e. the frequency of the systoles on the one hand and a display of the frequency of the ventricular extra-systoles on the other hand. For with the occurrence of ventricular extra-systoles, a more or less reduced ejection of blood from the heart occurs as a result of the premature contraction of the heart muscle, depending on the prematurity index. This is caused, i.a., by the fact that only an insufficient quantity of blood could flow back into the ventricle because the filling time was too short.

The cause or origin of such ventricular extra-systoles can be variable in nature, whereby, however, ventricular extra-systoles arise never from the normal conduction system of the heart, but, as the name says, from the ventricles.

If such ventricular extra-systoles occur frequently and/or very early after a systole of the normal heart activity, there exists the danger of a fibrillation of the heart which will cause death if no immediate resuscitation and defibrillation occurs. As may be seen from the above, the separate recording of the frequency of the ventricular extra-systoles is of substantial medical importance.

The normal frequency of heartbeats too, cleared from falsification by extra-systoles, ergo the pure frequency of systoles, is very important from the medical standpoint, for this frequency of heartbeats should always lie within a certain range which can vary individually depending on the physical constitution and the state of health of the particular person.

It is intended with the present invention to provide a cardiotachometer of the type cited at the start in such a way that it permits a differentiation between systoles and ventricular extra-systoles, so that the mean frequency of the systoles and extra-systoles in time can be measured separately.

A cardiotachometer for determining the frequency of heartbeats by means of an ultrasonic transmitting and receiving device working according to the ultrasonic Doppler-principle, with a signal-processing circuit arrangement connected downstream for the purpose of determining a movement of a vascular wall, by means of which the aforementioned task is solved, is distinguished pursuant to the invention by an additional ultrasonic transmitting and receiving device with an additional signal-processing circuit arrangement for the purpose of determining the speed of the blood flow, and a reference device connected downstream from the two ultrasonic transmitting and receiving devices and their signal-processing circuit arrangements for the purpose of determining a time coincidence of Doppler-output signals of these two ultrasonic transmitting and receiving devices.

Such a cardiotachometer makes possible the recording of systoles and ventricular extra-systoles of the heart with differentiation between these two kinds, by conducting the measurements of the Doppler-frequency mentioned above not directly on the heart, but for instance on an artery, for example the arteria radialis, whereby the differentiation between systoles and ventricular extra-systoles is made based on the fact that the systoles generate a pulse wave in the blood vessel, for example in an artery which is accompanied by a distinct movement of the wall of this blood vessel, whereas the ventricular extra-systoles result only in a socalled displacement wave in the blood vessel, in which no noticeable movement of the wall of this blood vessel occurs. If a pulse-like Doppler blood flow velocity measurement signal obtained by the measurement of the blood flow velocity coincides in time with a pulse-like Doppler-signal of the movement of the vascular wall obtained by determination of the movement of the vascular wall, a systole is present, whereas in the absence of a simultaneous Doppler-signal of the movement of the vascular wall the Doppler blood flow velocity signal corresponds to a ventricular extra-systole. This differentiation is carried out in the aforementioned reference device which delivers a pulse-like output signal corresponding to a systole counting pulse preferably only when there occurs simultaneously a Doppler blood flow velocity signal and a Doppler vascular wall movement signal.

Although blood flow measuring instruments, by means of which the velocity of the blood flow in blood vessels can be measured with the ultrasonic Doppler-effect method, are known per se, for instance, from the German examined patent specification Nos. 1 791 191, 2 159 129 and 2 159 130, as well as from the German unexamined patent specification No. 2 402 407, the present invention is not aimed at the measurement of the blood flow velocity as such.

The cardiotachometer pursuant to the invention is preferably designed in such a way that the ultrasonic transmitter of the ultrasonic transmitting and receiving device for the determination of the blood flow velocity is tuned to an ultrasonic frequency in the range of 5 to 10 MHz, preferably 5 MHz, while the ultrasonic transmitter of the ultrasonic transmitting and receiving device for the determination of the movement of the vascular wall is tuned to an ultrasonic frequency in the range of 1 to 3 MHz, preferably to one of 1 MHz. The ultrasonic receivers can be tuned in a corresponding manner.

By means of these two different frequencies, one of which is substantially greater than the other, the blood flow velocity and the movement of the vascular wall can be obtained separately and to a sufficient degree.

According to the invention, the cardiotachometer circuitry can be designed in that way that the signal-processing circuit arrangement, which is connected downstream from the ultrasonic transmitting and receiving device for determination of the blood flow velocity, is a first pulse-generating device, in particular a rectangular pulse-generating device responding to the ultrasonic Doppler-frequency signals in that manner that it generates one pulse each for every ultrasonic Doppler-frequency signal caused in a blood vessel as the result of a pulse wave and a displacement wave, and the signal-processing circuit arrangement which is connected downstream behind the ultrasonic transmitting and receiving device for the determination of a movement in a vascular wall, can be designed in that way that it is a second pulse-generating device, especially a rectangular pulse-generating device which generates one impulse each for every ultrasonic Doppler-frequency signal caused by a movement of the vascular wall which in turn was brought about by a pulse wave in a blood vessel. These pulses, which are preferably rectangular pulses, are fed to the reference stage which in the simplest case is an AND gate emitting a signal at its output only if a pulse occurs simultaneously at the output of the first and second pulse-generating device, so that the output signal of the reference stage is thus in every case a systole counting pulse which, if necessary, can still be differentiated.

In addition, the pulses appearing at the output of the first pulse-generating device by circumventing the reference stage, can, if need be after they have been differentiated, be utilized as systole- and extra-systole counting pulses, and the number of the ventricular extra-systoles may be obtained from the difference between the systole counting pulses and the systole and extra-systole counting pulses.

The two ultrasonic transmitting and receiving devices may be combined advantageously in a measuring head, whereby the ultrasonic transmitters are arranged in the center of a cross-sectional area of the measuring head running in parallel to a coupling membrane for coupling to the body surface of the user, while the ultrasonic receivers are divided each into several, preferably at least three individual ultrasonic receivers connected in parallel to each other and relatively small in dimension compared to the ultrasonic transmitters which are preferably arranged symmetrically around the ultrasonic transmitters. The receivers, for instance piezoelectric crystals which serve to pick-up the movement of the vascular wall, may hereby be focused and seated on a soft support on their backside for the pick-up of the blood flow velocity, in contrast to the rigidly seated receivers, for example piezoelectric crystals.

Other developments of the invention are cited in the subclaims and illustrated in the following specification of figures.

The invention is illustrated in greater detail hereinafter with regard to a particularly preferred form of construction, and is illustrated in the accompanying drawings, wherein FIG. 1 is a block circuit diagram of an embodiment of a cardiotachometer pursuant to the invention, whereby, however, the representation of the power supply of the individual units was omitted for reasons of a clearer illustration of the way this cardiotachometer functions;

FIG. 2 is a schematic representation of the power supply of the individual units of the cardiotachometer according to FIG. 1, whereby for reasons of simplification only some units of this cardiotachometer are represented, while the power supply of the remaining units is only indicated by arrows;

FIG. 3 illustrates the waves of an electrocardiogram with a systole and an arbitrarily assumed extra-systole, as well as a pulse wave and a displacement wave occurring as a result of the systole and, respectively, extra-systole of the heart in an artery, and the movement of the vascular wall of the artery in which the pulse wave occurs, as well as individual signals generated in the cardiotachometer of FIG. 1 pursuant to the invention based on the pulse wave, the displacement wave and the movement of the vascular wall, whereby the horizontal axis represents the progress with respect to time, and this progress with respect to time coincides in the individual parts I to VIII of FIG. 3;

Figure 1:
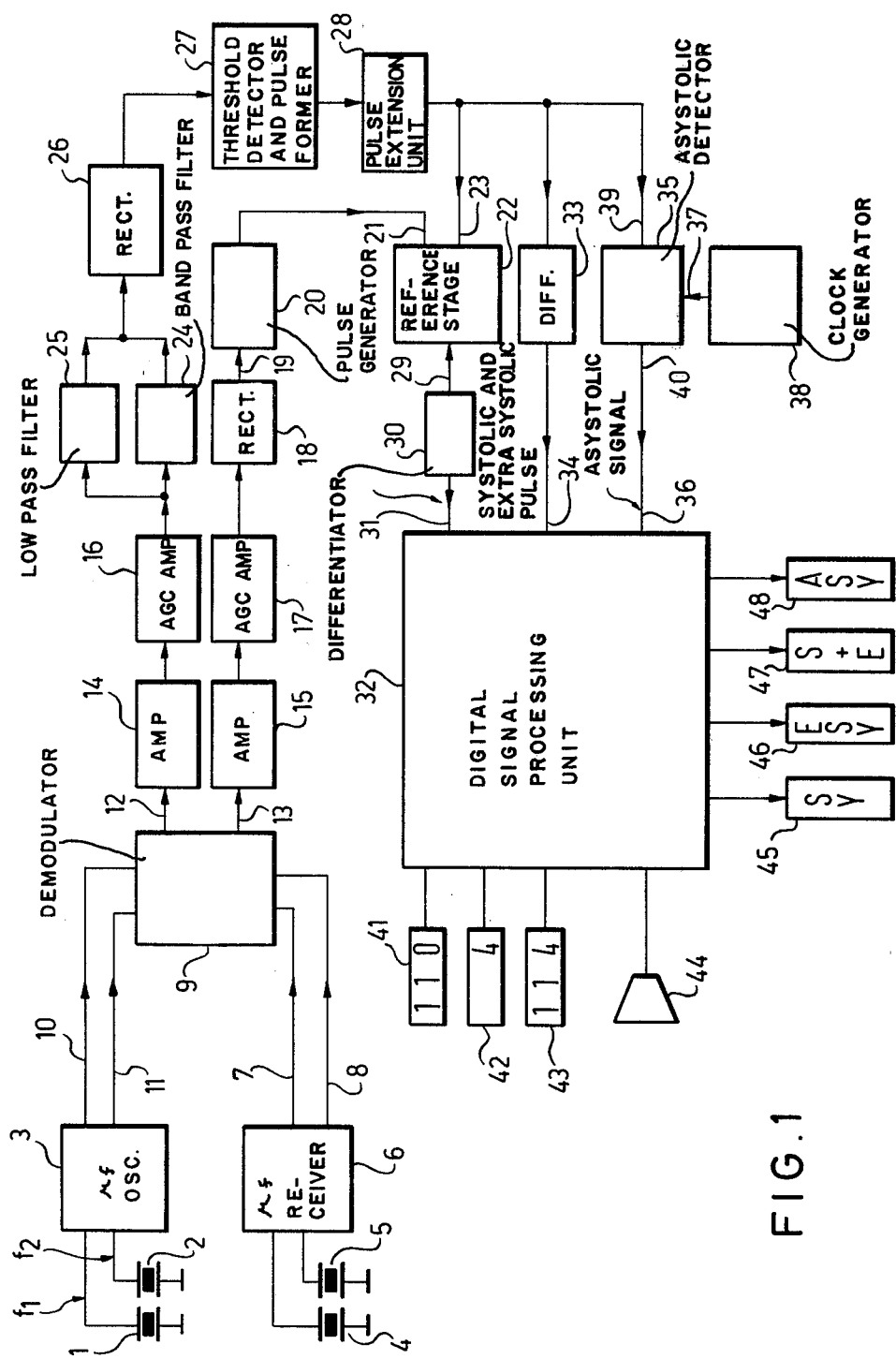

Reference is made at first to FIG. 1 whereby the embodiment of a cardiotachometer shown therein has a first ultrasonic transmitter 1 and a second ultrasonic transmitter 2 which may be, for example, barium titanate resonators. The ultrasonic transmitters 1 and 2 are coupled to a radio-frequency oscillator unit 3. This radio-frequency oscillator unit 3 generates continuous high-frequency oscillations of two different frequencies, namely of a first frequency $f_1$ which lies in the range of 5 to 10 MHz and amounts preferably to 5 MHz, as well as of a second frequency in the range of 1 to 3 MHz, preferably of 1 MHz.

The radio-frequency oscillations of the frequency $f_1$ are delivered to the ultrasonic transmitter 1 and the ultrasound of the same frequency reflected as a continuous wave train by this ultrasonic transmitter serves the purpose of determining the velocity of the blood flow by ultrasonic Doppler-frequency measurement. The ultra-sound is directed for this purpose by the ultrasonic transmitter 1, for instance, to an artery in which the blood pulsates according to the heartbeats of the person in which the blood flow velocity is being measured. The blood flow velocity shall hereby not be measured with an absolute value, but the heart-frequency shall rather be obtained, i.e. counting pulses shall be generated, each of them corresponding to a systole of the heart.

The radio-frequency oscillations of the frequency $f_2$ are delivered to the second ultrasonic transmitter 2 which converts them into continuous ultrasonic wave trains of the same frequency. These ultrasonic wave trains serve the purpose of determining the deformation of a blood vessel or of the tissue caused by the systoles of the heart, and thus the detection of the movement of the wall by ultrasonic Doppler-frequency measurement. To this end, the ultrasonic transmitter 2 is directed, for instance, to the artery in which the velocity of the blood flow is being measured, namely preferably to the same site of the artery, at which the measurement of the velocity of the blood flow mentioned previously takes place.

Furthermore, the cardiotachometer according to FIG. 1 comprises a first ultrasonic receiver 4 and a second ultrasonic receiver 5 which may consist each of several individual ultrasonic receivers 501, 502, and 503, and, respectively, 401, 402, and 403 (see FIGS. 4 and 5), and which, as explained further below, are arranged in a common measuring head together with the first and second ultrasonic transmitters 1 and, resepctively 2. These ultrasonic receivers 4 and 5 which convert the ultrasonic oscillations received into electric radio-frequency signals, may be, for instance, barium titanate resonators.

The two ultrasonic receivers 4 and 5 are coupled to a radio-frequency receiver unit 6 which is designed and tuned in such a way that it delivers on a first output line 7 the radio-frequency oscillations of the frequency $f_1$ which are modulated with a first Doppler-frequency $\Delta f_1$, the latter being in turn a function of the flow velocity of the blood, whereby this Doppler-frequency $\Delta f_1$ is largely proportionate to the flow velocity of the blood. In addition, the radio-frequency receiver unit 6 delivers an electric radio-frequency signal of the frequency $f_2$ on a second output line 8 which is modulated with a second Doppler-frequency $\Delta f_2$ resulting from the movement of the vascular wall, the Doppler-frequency $\Delta f_2$ being generally a monotonous function of the movement of the vascular wall, whereby it is essential that a genuine deformation of the blood vessel and, respectively, of the movement of the vacular wall is determined only qualitatively by this Doppler-frequency $\Delta f_2$, with their magnitude lying above a certain threshold.

The output lines 7 and 8 of the radio-frequency receiver unit 6 lead to a demodulator unit 9 which is supplied in addition by radio-frequency oscillations of the frequencies $f_1$ and $f_2$ from the radio-frequency oscillator unit 3 by way of the output lines 10 and 11. The radio-frequency carrier wave of the frequency $f_1$ and, respectively, $f_2$ is removed in the demodulator unit 9, so that the Doppler-frequency-signal $\Delta f_1$ emerges at a first output 12 of the demodulator unit 9, while the Doppler-signal $\Delta f_2$ can be taken off a second output 13 of this demodulator unit. It should be pointed out here that both the positive and negative $\Delta f_1$ and $\Delta f_2$ signals may be used for evaluation and, respectively, further processing in the circuit arrangement according to FIG. 1, although positive $\Delta f_1$ and $\Delta f_2$ signals are preferably evaluated in the present case. The $\Delta f_1$ signal is amplified by way of a first amplifier 14, while the $\Delta f_2$ signal is amplified by way of a second amplifier 15. An automatic gain control (AGC) amplifier 16 or, respectively, 17 with a peak value detector is connected downstream behind each of these two amplifiers 14 and 15, so that wave trains whose signal voltage is brought to approximately the same level by the AGC amplifiers and whose frequency equals the Doppler-frequency $\Delta f_1$ and, respectively, $\Delta f_2$ each, are obtained at the outputs of these AGC amplifiers 16, 17. It should be pointed out at this place that the Doppler-frequencies $\Delta f_1$ and $\Delta f_2$ are of course not exactly discrete frequencies but comprise an entire frequency spectrum each because the blood flow velocity and the velocity of the movement of the vascular wall consist also of a whole spectrum of velocities, so that of necessity also an entire spectrum of Doppler-frequencies is produced respectively.

Figure 3:
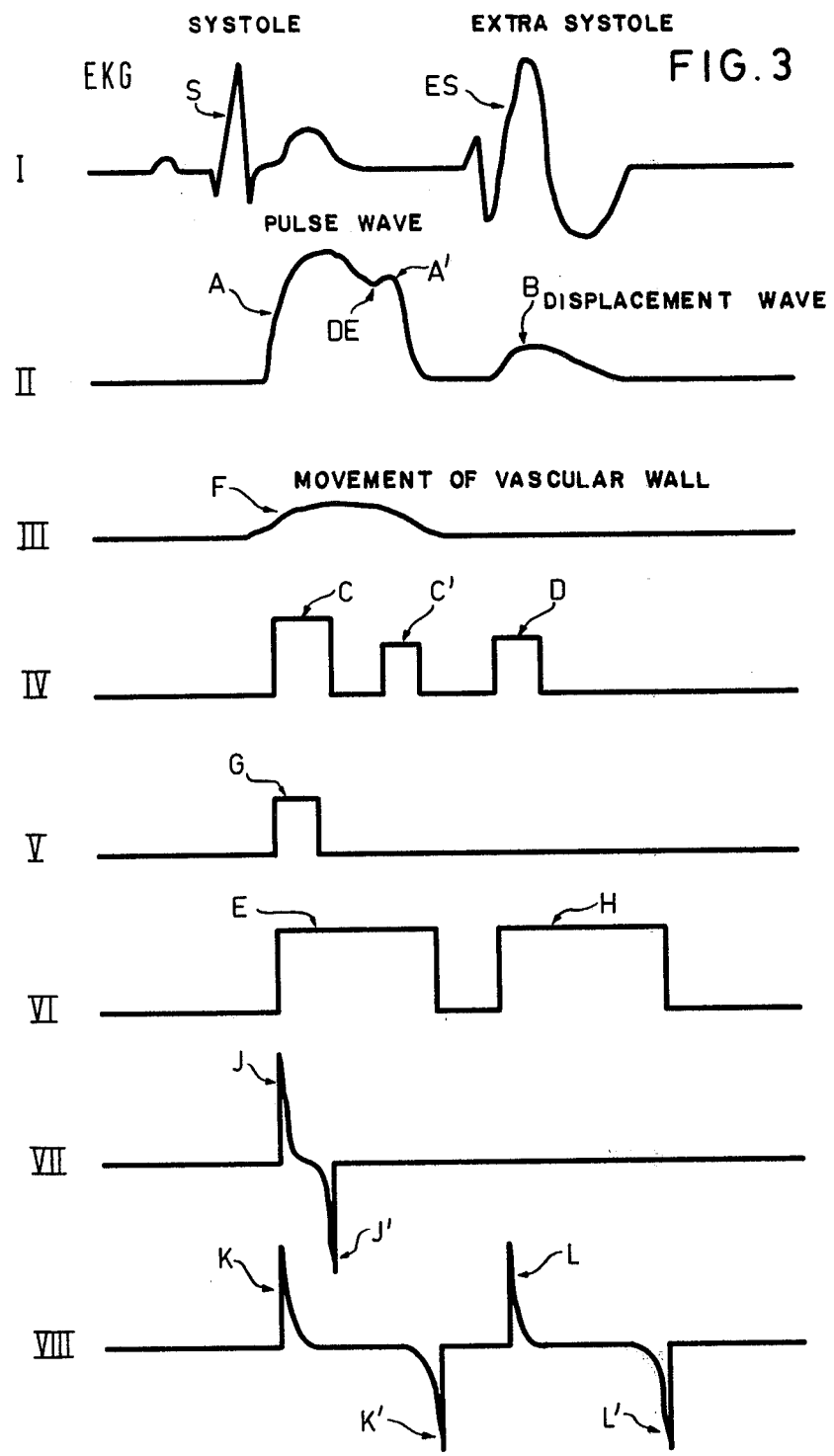

A rectifier 18, at the output 19 of which the signal F shown at III in FIG. 3 is obtained and which represents the movement of the vascular wall, is connected downstream behind the AGC amplifier 17. This signal F is converted by a threshold value detector- and pulse-forming unit 20 connected downstream from the rectifier 18 into a rectangular pulse G shown at V in FIG. 3. The output of the threshold detector- and pulse-forming unit 20 is connected with a first input 21 of a reference stage 22 dealt with in greater detail further below, after it is discussed at first in greater detail hereinafter in what manner the signals appearing at the output of the AGC amplifier 16 are processed to input signals for the second input 23 of the reference stage 22.

In order to understand the further signal-processing following the AGC amplifier 16, it is first of all necessary to deal in greater detail with the parts I and II of FIG. 3. I in FIG. 3 represents part of an electrocardiogram which was recorded by some electrocardigraph and exhibits the progression of a curve S corresponding to a systole of a human heart, as well as a subsequent curve progession ES corresponding to an arbitrarily assumed extra-systole which may follow the systole after a certain time interval. Whereas the systole of the heart corresponds to a pulse wave in an artery, an extra-systole results only in a socalled displacement wave in the artery. The spectrum of the Doppler-frequencies of a pulse wave differs substantially from the spectrum of the Doppler-frequencies of a displacement wave, whereby the frequencies of the erstwhile spectrum lie in the range of 700 to 1800 Hz, while the frequencies of the latter spectrum lie in the range of about 0 to 500 Hz. In order to eliminate undesirable disturbing noises which are also termed artifacts and may be caused, for instance, by scratching or be radio noises, a band-pass filter permitting only the passing of frequencies of 700 to 1800 Hz is connected downstream behind the AGC amplifier 16 for the purpose of filtering out the frequency spectrum which corresponds to the Doppler-frequencies caused by a pulse wave.

In addition, a low-pass filter arranged in parallel to the band-pass filter 25 and allowing the frequencies to pass which lie in the frequency spectrum of the Doppler-frequencies corresponding to a displacement wave, is connected downstream behind the AGC amplifier 16. This low-pass filter has a pass-band of 0 to 500 Hz. Although a number of interfering noises can occur also within this range, the fact as to whether an interference noise or a genuine signal caused by a displacement wave is present can be ascertained by establishing whether or not a pulse wave occurred immediately prior to it. So as not to complicate the present embodiment unnecessarily, a respective circuit is not shown in the drawing, especially since such an additional circuit can be dispensed with in many cases because of its insignificant interference noise level.

A joint rectifier 26 is connected downstream behind the band-pass filter 24 and the low-pass filter 25, at the output of which appear the signals A and B represented under II in FIG. 3, the former corresponding to a pulse wave and the latter to a displacement wave. The signal identified overall by A may exhibit in addition a signal part A' which will be dealt with subsequently in greater detail. Since the signals A and B can occur always consecutively and never simultaneously, it is unnecessary to connect a separate rectifier each behind the band-pass filter 24 and the low-pass filter 25, but, as mentioned above, the joint rectifier 26 will suffice.

The rectifier 26 is followed by a threshold value detector- and pulse-forming unit 27 which converts the signals A and B into regular pulses, causing the rectangular pulses C and D as shown in FIG. 3 under IV and, if necessary, also the rectangular pulse C', which corresponds to the progression curve A', to appear at the output of this threshold detector- and pulse-forming unit. The signal part A' which leads to an additional rectangular pulse C', is caused in that way that the pulse wave normally exhibits an intermediate minimum DE called dicrotism and stemming from the closure of the aorta cardiac valve. This dicrotism may be practically absent when valve insufficiencies exist. The rise following the dicrotism DE to which the signal part A' corresponds, may be larger or smaller depending on the elasticity of the respective heat and of the peripheral vascular system. A marked dicrotism occurs in any case generally with the normal, healthy human heart, causing in these cases the emergence of an additional rectangular pulse C' at the output of the threshold detector- and pulse-forming unit 27.

This additional rectangular pulse C' is undesirable, however, because the aim is to obtain a signal rectangular pulse for each pulse wave corresponding to a systole in order to be able to count the systoles clearly, independently of the respective individual user of the cardiotachometer. For this reason, a pulse extension unit 28 is connected downstream from the threshold detector- and pulse-forming unit 27, the former extending the rectangular pulse C to a width of 300 msec, so that the rectangular pulse E shown in FIG. 3 at IV is obtained which so to speak has "gobbled up" the additional rectangular pulse C'. The pulse width of 300 msec results from the fact that the maximum width of the pulse wave with respect to time does not exceed the value of 300 msec, so that an additional rectangular pulse C', which may possibly exist with all potentially occurring pulse waves, is "gobbled up" by the rectangular pulse E. This rectangular pulse E and the rectangular pulse D which is of necessity widened also to 300 msec to the rectangular pulse H and corresponds to a displacement wave, are placed at the second input 23 of the reference stage 22.

The reference stage 22 can, for instance, be an AND-gate with the two inputs 21 and 23, one of which receives the signal shown in FIG. 3 at V and the other the signals indicated in FIG. 3 at VI. As a result, a signal in the form of a rectangular pulse is obtained at the output 29 of this AND-gate or, respectively, the reference stage 22 only if the signals G and E appear simultaneously, i.e. if a genuine pulse wave occurs which is characterized by the fact that a marked movement of the vascular wall takes place simultaneously with it. If however the signal H appears which corresponds to a displacement wave characterized by the fact that no marked movement of the vascular wall takes place simultaneously with the latter, then no signal will appear at the output 29. Since a pulse wave corresponds to a systole and a displacement wave to an extrasystole, a rectangular pulse which is differentiated in a differentiating stage 30 is obtained at the output 29 only for each systole, so that at a first input 31 of a digital signal-processing unit 32 to which the output of the differentiating stage 30 is connected, a positive and a negative needle pulse is obtained, of which only the former is effective, however, as a counting pulse because the electronics connected to the input 31 in the digital signal-processing unit 33 is suitably triggered at the side. The systole-counting pulses are therefore obtained in effect at the input 31.

The output of the pulse-extending unit 28 is connected besides to another differentiating stage 33, with its output connected to a second input 34 of the digital signal-processing unit 32. The differentiating stage 33 differentiates between the rectangular pulses E and H so that a positive and a negative needle pulse K and K' respectively, as well as L and L' respectively are obtained at the input 34 for each rectangular pulse E and H, whereby, because of the respective triggering of the edge of the electronics of the digital signal-processing unit 32 following the input 34, only the positive needle pulses K and L become effective. The latter form therefore in effect systole- and extra-systole-counting pulses with the result that the sum of the pulses becoming effective at the input 34 equals the sum of systoles and extra-systoles occurring in the carrier of the cardiotachometer.

Finally, the output of the pulse-extending unit 28 is connected furthermore to the input of a socalled asystolia detector 35. This asystolia detector 35 delivers always a signal at its output, which is connected to a third input 36 of the digital signal-processing unit 32, if neither a systole nor an extra-systole occurs during a predetermined period preferably selected with 1200 msec, i.e. if neither a rectangular pulse E nor a rectangular pulse H is delivered at the input of the asystolia detector 35. For this purpose, the asystolia detector 35 can be constructed, e.g., as a counter receiving continuous pulses from a clock signal generator 38 at a counter entry 37, whereby its input 39 which is connected with the pulse-extending unit 28, is the reset input of the counter, while the output 40 of the asystolia detector which is connected to the input 36 of the digital signal-processing unit 32, is then the counting output of this counter where a signal appears only if a predetermined counting value is reached corresponding to a nonoccurrence of systoles and extra-systoles during a predetermined period of, say, 1200 msec. This counting value which results in the delivery of a signal at the output 40, is 1200 in the example given, provided the clock signal generator 38 delivers one counting pulse per millisecond to the counter entry 37, since the counting value 1200 will only be reached if the counter forming the asystolia detector 35 is not reset within a period of 1200 msec by a rectangular pulse E or H. The signal appearing at the output 40 is hereinafter also termed an asystolia signal.

The digital signal-processing unit 32 does not require detailed description since it may in principle be a computer with a time measurement device and its structure is easily recognized by the expert from the functions explained hereinafter.

In the embodiment shown, the digital signal-processing unit 32 must perform the following functions based on the signals appearing at the inputs 31, 34 and 36:

(1) determine the heart pulse frequency and transmit it to a first display device 41, on which it is displayed in beats per minute. In the present example, the display device 41 just indicates 110 heartbeats per minute. This heart pulse frequency can be determined by measuring the time interval between two systoles in the digital signal-processing unit on the basis of the systole counting pulses obtained at the input 31. The heart pulse frequency is generally between about 40 and about 180 beats per minute.

(2) The digital signal-processing unit 32 determines furthermore the number of extra-systoles occurring on the average during a predetermined period. This mean number of extra-systoles per minute is displayed digitally on a second display device 42. In order to emphasize the medical importance of this magnitude, it should be pointed out that, if only very few extra-systoles occur, for instance on the average a single extra-systole per hour, the person using the cardiotachometer is still safe. If, however, for instance, seven extra-systoles occur on the average in one minute, this person is endangered. According to the representation shown by way of example in FIG. 1, the display device 42 is just indicating that an average of four extra-systoles occur per minute. This number of extra-systoles can be obtained in connection with the time measurement, as can readily be seen, from the difference between the pulses obtained at the input 31 and at the input 34.

(3) In addition, the digital signal-processing unit 32 shall display the number of systoles and extra-systoles occuring at an average per time unit on a third display device 43. This indicated value equals, if the indicated values appearing on the display devices 41 and 42 relate to the same time unit, the sum of the last two indicated values. In the present example, the sum of systoles and extra-systoles per minute equals therefore on the average 114.

(4) An alarm signal shall be generated if the heart pulse frequency lies outside an adjustable range which differs individually. This alarm signal can be generated as an acoustical signal by means of a loudspeaker 44. Since, however, various alarm signals shall be produced and the user of the cardiotachometer shall always be in the position to determine equivocally which state of alarm exists at the precise moment, a first optical alarm display device 45 is provided in addition, on which, for instance, the display "SY" appears when the heart pulse frequency lies below or above the adjustable range mentioned above. This adjustable range in a healthy person is, for instance, 40 to 180 heartbeats per minute, so that an alarm signal is triggered for this person only when the heart pulse frequency is lower than 40 or higher than 180. In contrast, the admissible range of the heart pulse frequency of a person injured by an infarction can be such that it is necessary to trigger an alarm signal already when the heart pulse frequency is less than 70 or more than 120.

(5) The digital signal-processing unit 32 shall furthermore trigger an alarm signal when the mean number of the extra-systoles exceeds a predetermined value, for instance one that exceeds six extra-systoles per minute. This alarm signal is also generated acoustically by the loudspeaker 44 and is at the same time displayed on a second optical alarm display device 46, in that, for instance, the display "ESY" appears on the latter.

(6) Finally, an alarm signal is to be triggered if the the sum of systoles and extra-systoles occurring on the average per time unit exceeds a predetermined value. Besides being sounded by the loudspeaker 44, this alarm signal is displayed also by a third optical alarm display device 47, on which in such a case, for instance, the display "S+E" is shown. This mean number of systoles plus extra-systoles can, e.g., be that number which occurs on the average during five normal heartbeats.

(7) Finally, an alarm signal shall be given if no systole and extra-systole is present at all during a predetermined period of, e.g., 1200 msec. For all practical purposes, this signal is the asystolia signal occurring at the input 36 which is delivered acoustically by the loudspeaker 44 and optically by a fourth alarm displaying device 48, whereby the display "ASY" appears, e.g., on the latter in case of an alarm.

Although three different digital display devices 41, 42 and 43 are shown in FIG. 1 for reasons of clearer representation, a single digital display device may be employed instead, on which appear optionally the individual values to be indicated, for instance by depressing a button or automatically in periodic sequence.

The optical alarm display devices 45, 46, 47 and 48 too, may be substituted, as is preferable if for no other reason than space and cost, by a single optical alarm display device which displays in case of an alarm, respectively, the symbols "SY" or "ESY" or "S+E" finally "ASY".

Figure 2:
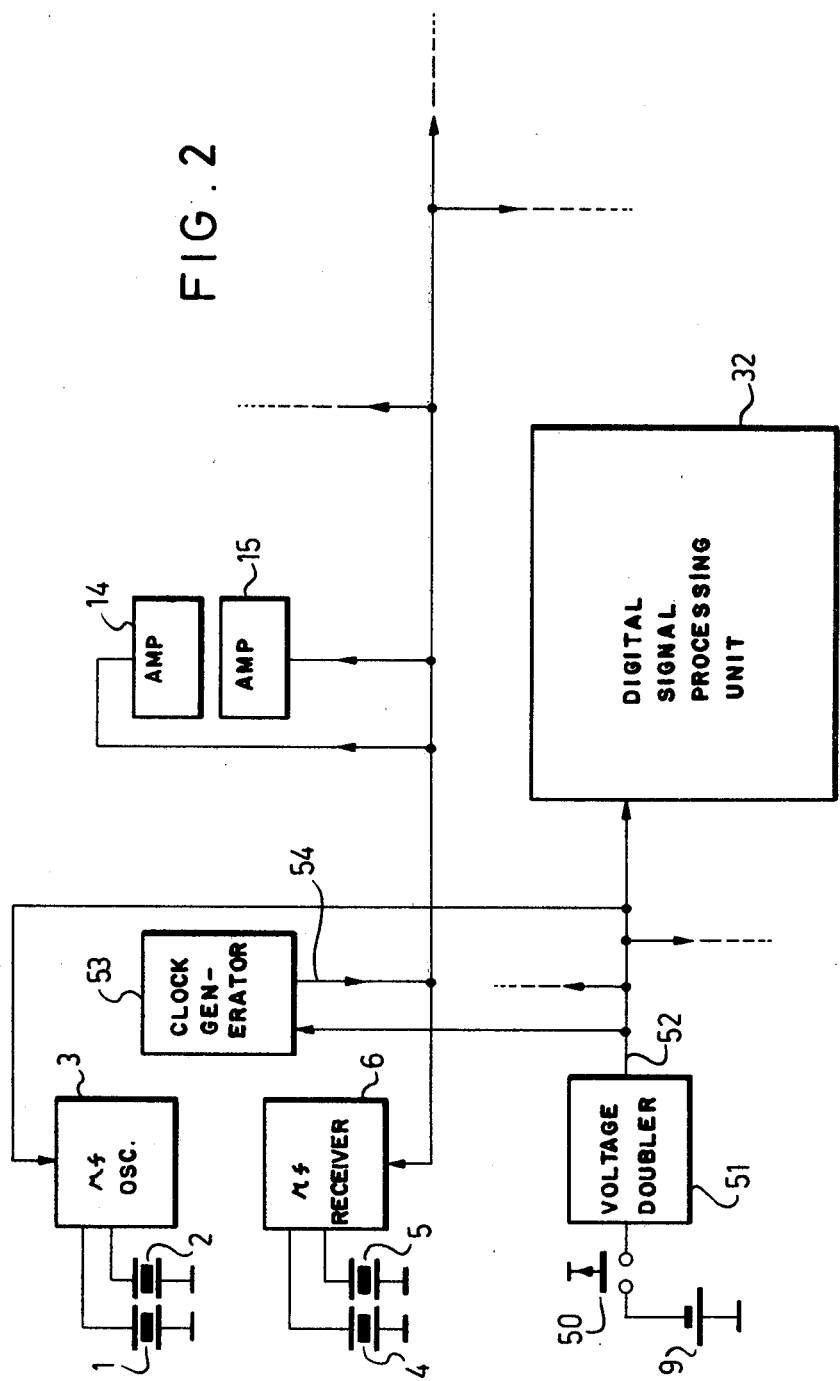

FIG. 2 shows a schematic representation of the current supply for the cardiotachometer shown in FIG. 1. This current supply comprises, as the cardiotachometer is preferably designed in the form of a wristwatch, a small battery, for instance a lithium battery. This battery 49 is connected by way of a switch 50, for instance a pushbutton switch, with a voltage doubler 51 which is provided because the voltage of the lithium battery of only 2.6 V is insufficient for driving the individual circuit units of the cardiotachometer. The output 52 of the voltage doubler 51 is connected on the one hand with all the circuit units shown in FIG. 1 which should be connected to their operating voltage, for instance the radio-frequency oscillator unit 3 and the digital signal-processing unit 32. On the other hand, the output 52 of the voltage doubler 51 is connected to the input of a clock unit 53, with the supply voltage for other circuit elements of the cardiotachometer according to FIG. 1 being connected at the output 54 in heart frequency time only during the periods in which the systoles and extra-systoles can occur. In contrast, the supply voltage at output 54 is turned off during the remaining time in order to give the battery 49 a longer useful life. In order to make clear the attainable advantage, it should be pointed out that the mean time elapsing between the end of a pulse and the beginning of the consecutive pulse wave is about 500 msec. Proceeding furthermore on the assumption that extra-systoles occur shortly after a normal systole, a substantial reduction in current consumption of the cardiotachometer can be attained through the clock unit 53.

The elements connected to the output 54 of the clock unit 53 are, e.g., the radio-frequency receiving unit 6, the demodulator unit 9, the two amplifiers 14 and 15, the band-pass filter 24, the rectifier 26, the threshold value detector- and pulse-forming unit 27 and the differentiating stage 30.

Beyond that, additional circuit units as shown in FIG. 1 can also be connected to the output 54.

It is generally possible to turn the current supply off for about one third of the measuring time, to the extent that it is turned on and off by way of the clock unit 53.

The circuit of the cardiotachometer according to FIG. 1 can be modified in various ways within the scope of the invention. It is thus possible, instead of feeding counting-pulses of systoles and extra-systoles to the input 34 of the digital signal-processing unit 32, to deliver only counting-pulses of extra-systoles of this input by processing the signals emerging at the output of the band-pass filter 24 and at the output of the low-pass filter 25 separately. This can be accomplished, for instance, in that way that only the signals appearing at the output of the band-pass filter 24 are processed further by way of the rectifier 26 and the threshold value detector- and pulse-forming unit 27, as well as the pulse-extending unit 28, and that the output of the pulse-extending unit 28 is connected with the input 23 of the reference stage 22 and the input 39 of the asystolia-detector 35, but not with the input of the differentiating stage 33; whereas, on the other hand, the signals emerging at the output of the low-pass filter 25 are processed further by way of a separate rectifier and a separate threshold detector- and pulse-forming unit connected downstream from the former, whose output is connected with the input of the differentiating stage 33. This embodiment is however somewhat more expensive than the form of construction of the cardiotachometer shown in FIG. 1, because subtraction of the number of systole counting pulses appearing at the input 31 from the number of systole- and extra-systole counting pulses appearing at the input 37 in the digital signal-processing unit for the purpose of determining the number of extra-systoles requires less circuit expenditure and energy consumption than an additional rectifier and an additional threshold value detector- and pulse forming unit.

In addition, the asystolia detector 35 and the clock signal generator 38, which are shown separately because of their special importance, can be included in the digital signal-processing unit 32, whereby the asystolia detector 35 is then reset each time by the systole- and extra-systole counting pulses.

Figure 4:
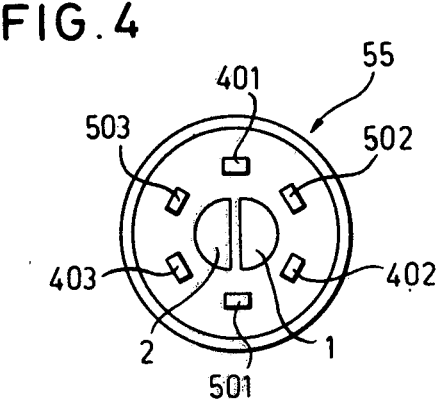
FIG. 4 is a schematic plan view of a measuring head exhibiting two ultrasonic transmitters and several ultrasonic receivers.
Figure 5:
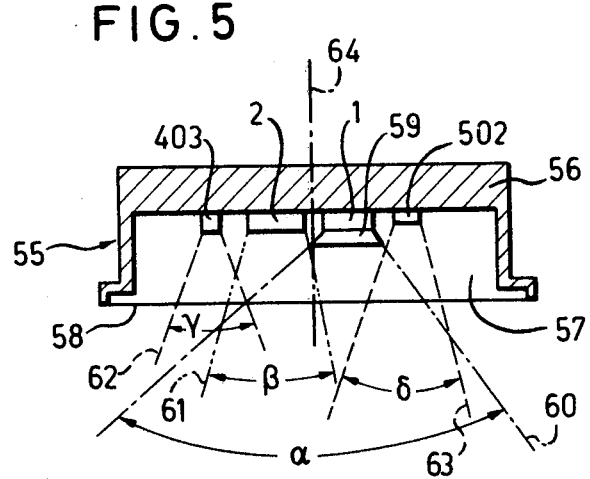
FIG. 5 is a sectional view of the measuring head of FIG. 4, in which the reflection- and receiving angles of the ultrasonic transmitters and receivers are indicated.
Figure 6:
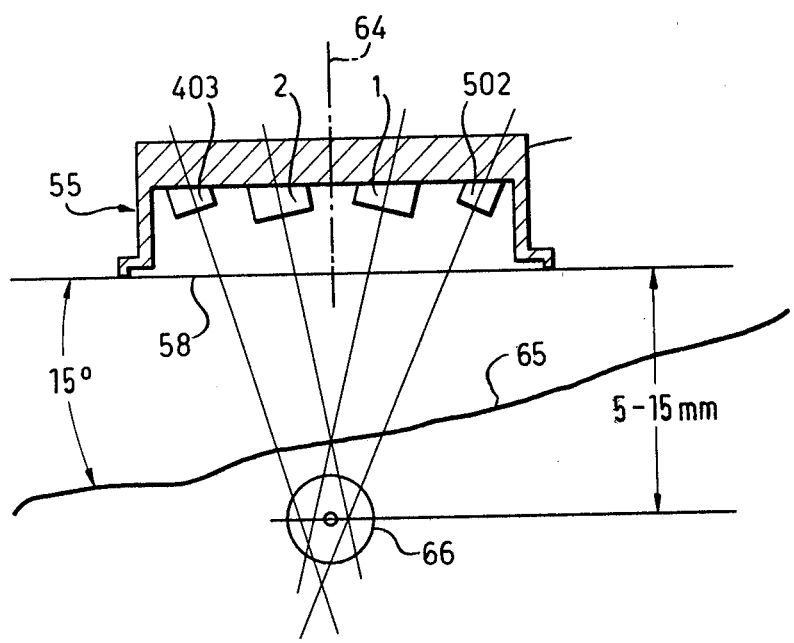
FIG. 6 is a sectional view of a similar measuring head with a skin surface drawn below it at a distance from the latter.

Reference shall be made here to the FIGS. 4 and 5 which represent a preferred embodiment of a measuring head 55 comprised of the first ultrasonic transmitter 1, the second ultrasonic transmitter 2, as well as the first ultrasonic receiver 4 and the second ultrasonic receiver 5 of the cardiotachometer, whereby the first ultrasonic receiver 4 consists of preferably at least three ultrasonic receivers 401, 402 and 403 connected in parallel, and the second ultrasonic receiver 5 also preferably of at least three ultrasonic receivers 501, 502 and 503 connected in parallel.

The ultrasonic transmitters 1 and 2 are transducer elements exhibiting a relatively large surface, preferably piezoelectric crystals, designed, e.g., in an approximately semicircular shape and arranged in the center of the cross-sectional area of the measuring head 55 which faces the skin surface of the carrier. In contrast, the ultrasonic receivers 401, 402 and 403, as well as 501, 502 and 503 are transducers with a relatively small surface, preferably piezoelectric crystals arranged in regular intervals about the two ultrasonic transmitters 1 and 2 and preferably each symmetrically by itself, so that the individual ultrasonic receivers in the embodiment shown are distributed equidistantly along the circumference of a circle, whereby the ultrasonic receivers 401, 402 and 403 are positioned at the tips of a first equilateral triangle, while the ultrasonic receivers 501, 502 and 503 are arranged at the tips of a second equilateral triangle.

The ultrasonic transmitters and receivers are fastened in a carrier body 56 and preferably cast into a carrier body 56 consisting of epoxy resin, since the latter quarantees a satisfactory insulation against vibration in the direction of the back of the measuring head 55 and provides good encapsulation of the ultrasonic transmitters and receivers. The ultrasonic transmitters and receivers project with their sides reflecting and receiving the ultrasound into a coupling medium 57 consisting, for instance, of oil or a gel. Finally, the measuring head 55 is sealed on the side facing the carrier of the cardiotachometer by a membrane 58 which establishes the skin contact with the carrier, and preferably by way of an additional coupling medium provided between the skin of the carrier and the membrane 58 of the measuring head 55. A lens 59, consisting preferably of plastic material, which widens the ultrasonic reflection cone 60 of the ultrasonic transmitter 1 to an aperture angle $\alpha$ of substantially more than 90°, preferably to 120°, is arranged in front of the transmitter 1 which serves to measure the flow velocity of the blood in one or several blood vessels. This guarantees on the one hand that a respective blood vessel, for example the arteria radialis and some other additional arterial vessels are with great probability exposed to ultrasonic waves without any special or too precise an attachment and localization of the cardiotachometer. Since the pulse wave to be measured occurs synchronously in all arterial vessels hit by the ultrasonic reflection cone 60, it does not matter that several arterial vessels are covered simultaneously, on the contrary, this is of advantage. The venous blood vessels exposed thereby involuntarily to ultrasonic waves don't interfere with their reflected ultrasonic energy because the flow velocities within these vessels are much lower and the Doppler-frequencies produced as a result remain thus outside of the medium frequency of the band-pass filter 24.

In contrast, the ultrasonic transmitter 2 serving the purpose of determining the wall movement of the respective blood vessel in which the pulse wave occurs, for instance the arteria radialis, has an ultrasonic reflection cone 61, the aperture angle $\beta$ of which being substantially less than 90° and preferably about 60°. Such a relatively acute aperture angle of the ultrasonic reflection cone 61 is necessary because no signals are to be accepted from muscle contractions of the forearm and in the carpal bone area (ulna, radius) but rather only those originating from the movement of the wall of the vessel under examination.

Furthermore, the ultrasonic transmitter 1 is arranged for the determination of the flow velocity preferably in such a way that its angle of slope runs backward (retrograde), i.e. that the scalar product of the sound propagation vector and the flow vector is less than 0, ergo that it is turned toward the heart and large vessels are being covered.

The ultrasonic receiving cone 62 of the ultrasonic receivers 401, 402 and 403, as well as the ultrasonic receiving cones 501, 502 and 503 are preferably not changed from their natural aperture angle $\gamma$ or $\delta$ of about 90°, but are fastened in their arrangement relative to the ultrasonic transmitters 1 and 2 at an angle of inclination of 15° to 30°, preferably of 15°, in relation to the center axis 64 of the measuring head 55 which runs at a right angle to the membrane 58. In this way it is accomplished that signals suitable for further processing are picked up with certainty when the measuring head is not exactly positioned above the blood vessel to be covered, for instance the arteria radialis. By variable seating of the wall and varying the resonance frequency of the ultrasonic receivers 401, 402, and 403 in relation to the ultrasonic receivers 501, 502 and 503, a cross-talk (acoustic coupling) and interference by harmonic waves is ruled out to a far-reaching degree.

It is claimed:

1. A cardiotachometer for determining heart-beat frequency comprising a first and a second doppler type ultrasonic transmitting and receiving device and a demodulator unit, said first ultrasonic transmitting and receiving device operating on a first frequency $f_1$ and providing at the output of the demodulator unit a first Doppler-frequency signal $\Delta f_1$ which is indicative of the vascular blood flow velocity; said second ultrasonic transmitting and receiving device operating on a second frequency $f_2$ lower than said first frequency $f_1$ and providing at the output of the demodulator unit a second Doppler-frequency signal $\Delta f_2$ which is indicative of the movement of the vascular wall; a first signal-processing circuit receiving as its input signal said first Doppler-frequency signal ($\Delta f_1$), a second signal-processing circuit receiving as its input signal said second Doppler-frequency signal ($\Delta f_2$), and a reference device receiving as its input signals the output signals of said first and second signal processing circuit, said reference device being adapted to deliver an output signal each time an output signal of said first signal processing circuit arrangement coincides with an output signal of said second signal processing circuit arrangement which is indicative of the heart-beat frequency.

2. The cardiotachometer according to claim 1 wherein the transmitter of the first ultrasonic transmitting and receiving device is operable at a frequency in the range of 5 to 10 and the transmitter of the second ultrasonic transmitting and receiving device is operable at a frequency in the range of 1 to 3 MHz.

3. The cardiotachometer according to claim 1 or 2, the first signal-processing circuit comprises a first rectangular pulse-generator device, generating one pulse each for each pulse wave and each displacement wave in the blood vessel; and the second signal-processing circuit comprises a second rectangular pulse-generator, generating one pulse each for every movement of the vascular wall caused by a pulse wave in the blood vessel.

4. The cardiotachometer according to claim 3 wherein each of the first and second pulse-generator has connected therewith, in series, the demodulator, an amplifier, a rectifier and a rapid value-detector and pulse forming unit.

5. The cardiotachometer according to claim 3, wherein the first pulse-generator includes a band-pass filter, and a low-pass filter connected in parallel, said band-pass filter having a pass-band of 700 to 1800 cps and said low-pass filter having a pass-band of 0 to 500 cps.

6. The cardiotachometer according to claim 3 wherein the first pulse-generator has a pulse extension unit for the elimination of separate pulses caused by a dicrotism in the pulse wave, whereby the duration of the pulse extension to which passing pulses are extended is about 300 msec.

7. The cardiotachometer according to claim 6 including a digital signal-processing unit having a first input connected by way of a differentiating stage with the output of the reference device.

8. The cardiotachometer according to claim 7 wherein the digital signal-processing unit is provided with a second input connected by way of the differentiating stage with the output of the pulse extension unit of the first pulse-generating device.

9. The cardiotachometer according to claim 8, wherein the digital signal-processing unit is provided with a third input connected with the output of an asystolia detector, the latter connected in turn with the output of the first pulse-generating device.

10. The cardiotachometer according to claim 9 wherein the digital signal-processing unit (32) has at least one display devices for the display of the frequency of at least one of the systoles or the systoles-plus-extra-systoles, and at least on of an acoustic and optical alarm indicating devices to deliver an alarm signal if the frequency of the systoles lies outside of a range capable of being set and/or if the frequency of the extra-systoles and/or of the systoles-plus-extra-systoles exceeds a predetermined value, and/or if neither a systole nor an extra-systole occur during a predetermined period.

11. The cardiotachometer according to claim 1 wherein the ultrasonic transmitting and receiving devices are combined in a detecting head, the transmitter of said ultrasonic device being arranged in the center of the cross-sectional area of the head and run in parallel to a membrane for contact with the body surface of the user, the receivers of each of said ultrasonic devices being divided into a plurality of individual receivers, connected in parallel to each other, said individual receivers being relatively small in dimension compared to the transmitters, said receivers being arranged symmetrically around the ultrasonic transmitters.

12. The cardiotachometer according to claim 11 wherein the first ultrasonic transmitters have a reflection cone having an aperture angle ($\alpha$) substantially greater than 90°.

13. The cardiotachometer according to claims 11 or 27 wherein the second ultrasonic transmitter has an ultrasonic reflection cone having an aperture angle ($\beta$) substantially smaller than 90°.

14. A cardiotachometer according to claim 11 wherein the individual receivers of the first ultrasonic transmitting and receiving device are arranged for the determination of the flow speed at an angle of inclination of 15° to 30°, and the individual receivers of the second ultrasonic transmitting and receiving devices are arranged at an angle of 30° to 45° from their main direction of sound reception to the body surface.

15. A cardiotachometer according to claim 14 including a power supply for the receivers of the first and second ultrasonic transmitting and receiving devices and for part of the two signal-processing circuits and a timing unit connected to said power supply to provide selected intermittant power to said receivers and signal-processing circuits.

* * * * *